(12) United States Patent
Takiguchi et al.

(10) Patent No.: US 6,491,847 B1
(45) Date of Patent: Dec. 10, 2002

(54) DISCOTIC LIQUID CRYSTAL AND ORGANIC ELECTROLUMINESCENCE DEVICE USING SAME

(75) Inventors: Takao Takiguchi, Tokyo (JP); Shinjiro Okada, Isehara (JP); Akira Tsuboyama, Sagamihara (JP); Shinichi Nakamura, Isehara (JP); Takashi Moriyama, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 177 days.

(21) Appl. No.: 09/665,406

(22) Filed: Sep. 20, 2000

(30) Foreign Application Priority Data

Sep. 21, 1999 (JP) ............................................. 11-267102

(51) Int. Cl.[7] ........................ C09K 19/32; C09K 11/06; C07C 22/02; C07C 50/18; C07D 487/16; H05B 33/14

(52) U.S. Cl. .................... 252/299.62; 349/69; 570/183; 570/187; 544/245; 552/208; 552/224; 552/266

(58) Field of Search ..................... 252/299.62; 428/1.1; 349/69; 570/183, 187; 544/245; 552/208, 224, 266; 136/263

(56) References Cited

U.S. PATENT DOCUMENTS

| 5,141,785 A | 8/1992 | Yoshinada et al. ............. 428/1 |
| 5,160,451 A | * 11/1992 | Eidenschink ........... 252/299.01 |
| 5,750,050 A | * 5/1998 | Goodby et al. ......... 252/299.62 |

FOREIGN PATENT DOCUMENTS

DE 4343412 * 6/1995

OTHER PUBLICATIONS

Journal of the American Chemical Society, vol. 104, No. 19 (1982), pp. 5245–5247.
Journal of the Chemical Communications, No. 24 (1985), pp. 1794–1796.
Discotic liquid crystals, S. Chandrasekhar and G.S. Ranganath, pp., 59–82.
Physical Review Letters, vol. 70, No. 4 (1993), pp. 457–460.
Nature, vol. 371 (1994), pp. 141–143.
Pramana, vol. 9, No. 5 (Nov. 1977), pp. 471–480.
Advanced Materials, vol. 8, No. 10 (1996), pp. 815–819.
English abstract of DE 4343412, 1995.*

* cited by examiner

Primary Examiner—Shean C. Wu
(74) Attorney, Agent, or Firm—Fitzpatrick, Cella, Harper & Scinto

(57) ABSTRACT

A novel class of discotic liquid crystals represented by the following formula was synthesized, and a layer thereof was incorporated in an organic electroluminescence device.

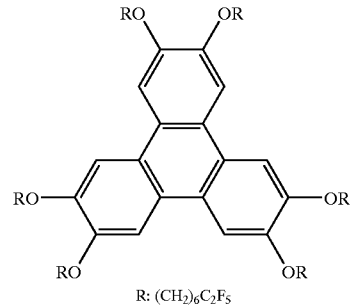

R: $(CH_2)_6C_2F_5$

7 Claims, 1 Drawing Sheet

DISCOTIC LIQUID CRYSTAL AND ORGANIC ELECTROLUMINESCENCE DEVICE USING SAME

BACKGROUND OF THE INVENTION

The present invention relates to a novel discotic liquid crystal having a polyfluorinated side chain and a broad and stable liquid crystal phase and to an organic electroluminescence device using the discotic liquid crystal.

Discotic liquid crystal phase is a liquid crystal phase discovered in 1977 by Chandrasekhar, et al. (Pramana, 9, 471 (1977)). As described in their paper entitled "Discotic Liquid Crystals" (Rep. Prog. Phys., 53, 57 (1990)) and in a paper entitled "Design and Synthesis of Discotic Liquid Crystal Molecules" by Shunsuke Takenaka (Japanese Chemical Society, Seasonal Publication, General Review, vol. 22, pp. 60+), the discotic liquid crystal phase is found in compounds having a disk-shaped core and a plurality of relatively long chains connected to the core. Such compounds may be classified into various types according to their core structure, inclusive of derivatives of hexa-substituted benzene and tri-substituted benzene; derivatives of phthalocyanine and porphyrin; derivatives of triphenylene, truxene and pyrylium, respectively; tribenzo-cyclononene derivatives, azacrown derivatives, and cyclohexane derivatives.

Based on the structural characteristic of a discotic liquid crystal, several reports have been made suggesting application thereof to devices. A systems including conjugated $\pi$-electrons, as found in derivatives of phthalocyanine or triphenylene, can provide a channel for electrons (or holes) (Piechocki, et al., J. Am. Chem. Soc., 104, pp. 5245 (1982)). Further, a system including an annular core, as found in an aza-crown derivative, can provide a molecular channel using the central spacing thereof as a selective molecular passage (Lehn, et al., J. Chem. Soc., Chem. Commun., pp. 1794 (1985)).

On the other hand, since 1987 when T. W. Tang et al. proved that a high luminance light emission was achieved by a low voltage drive of a laminate of their films of a fluorescent metal chelate complex and a diamine molecule, extensive research has been made on organic electroluminescence devices (hereinafter, the term "electroluminescence" is sometimes abbreviated as "EL" according to a common usage in the field) as luminescence or light emission devices having a high speed responsiveness and a high efficiency. An organic EL device is a carrier injection-type self-light emission device utilizing luminescence caused at the time of recombination of electrons and holes having reached the luminescence layer.

FIGS. 2 and 3 respectively illustrate a laminate structure of an ordinary organic EL device. Referring to FIG. 2 (or FIG. 3), an EL device includes a cathode metal electrode 21 (or 31) and an anode transparent electrode 24 (or 35) disposed on a transparent substrate 25 (or 36) for taking out luminescent light. Organic compound layers, each having a thickness on the order of several hundred Å (angstoms), are sandwiched between the electrodes. The cathode may generally comprise a metal having a small work function, such as aluminum, aluminum-lithium alloy, magnesium-silver alloy, etc. The anode may comprise a conductive material having a large work function, such as indium tin oxide (ITO). The organic compound layers, may ordinarily have a two layer structure including a luminescence layer 22 and a hole-transporting layer 23 as shown in FIG. 2 or a three layer structure including an electron-transporting layer 32, a luminescence layer 33 and a hole-transporting layer 34 as shown in FIG. 3.

The hole-transporting layer has a function of effectively injecting holes from the anode into the luminescence layer, and the electron-transporting layer has a function of effectively injecting electrons from the cathode into the luminescence layer. The hole-transporting layer also has a function of confining electrons, and the electron-transporting layer also has a function of confining holes, respectively, into the luminescence layer, i.e., carrier-blocking functions for enhancing the luminescence efficiency. For these carrier-transporting layers, inclusive of the hole-transporting layer and the electron-transporting layer, a charge-transporting performance, particularly a carrier mobility, may be regarded as an important property. An organic compound in an amorphous state may generally exhibit a carrier mobility on the order of $10^{-5}$ $cm^2/V.sec$, which cannot be said to represent a sufficient transporting performance. It is believed that if the mobility of a carrier-transporting layer is increased, a larger amount of carrier can be injected into the luminescence layer to enhance the luminescence efficiency, and simultaneously the thickness of the carrier-transporting layer (generally having a thickness on the order of several hundred Å) can be increased (to a thickness up to ca. 1 $\mu$m), so that it becomes possible to effectively prevent a short circuit between the electrodes sandwiching the organic layers and provide an improved productivity.

At present, in order to achieve a higher efficiency organic EL device, extensive work toward the development of various compound materials for the carrier-transporting layers has been made. Along with the activity, some proposal has been made to achieve a higher mobility by imparting mesomorphism to organic compounds forming carrier-transporting layers. Organic films generally used in organic EL devices are in an amorphous state and have no regularity regarding molecular alignment. In contrast thereto, some organic compounds in a liquid crystal state, i.e., having some order of molecular alignment, have been found to show a high mobility, thus calling attention.

For example, Haarer, et al. observed that a long chain triphenylene compound, a representative discotic liquid crystal material, exhibited a high hole mobility of $10^{-1}$ $cm^2/V.sec$ (Nature, vol. 371, p. 141 (1994)). Further, Haarer, et al. examined a relationship between hole mobility and molecular alignment order in columnar phase for a series of triphenylene-type discotic liquid crystals and reported that a higher order provided a higher mobility (Adv. Mater., vol. 8, p. 815 (1996)). Thus, a molecular alignment control advantageous for carrier transportation is expected to be achieved by utilizing spontaneous alignment of mesomorphic organic compounds, thus providing excellent carrier-transporting materials. On the other hand, organic EL devices involve problems regarding durability, such as deterioration of luminescence performance due to moisture and due to reaction between organic compound layers.

Some discotic liquid crystal compounds having polyfluorinated side chains have been reported in Liquid Crystal, vol. 19, No. 6, pp. 759–764 (1995). More specifically, three species of triphenylene derivatives (5a, 5b and 5c), each having 6 polyfluorinated side chains, are shown in FIG. 2 at page 760 of the above report. These compounds have an intermediate carboxyl group in their side chains and do not cause transformation from the discotic columnar phase to clarifying point (Iso), but reach a decomposition point on temperature increase as shown in a table at an upper left portion of page 761, so that they cannot be regarded as stable discotic liquid crystal compounds.

SUMMARY OF THE INVENTION

A generic object of the present invention is to solve the above-mentioned problems of the prior art.

A more specific object of the present invention is to provide a novel discotic liquid crystal compound having a stable and broad discotic liquid crystal phase.

Another object of the present invention is to provide an organic electroluminescence device exhibiting stable and good luminescence performance by using the liquid crystal compound.

According to the present invention, there is provided a discotic liquid crystal compound represented by formula (1) below:

Ar$-$(X$-$R)$_n$          (1), wherein Ar denotes a group of 2,3,5,6-benzoquinone-tetra-yl, 2,3,4,6,7,8-anthraquinone-hexa-yl, 2,3,6,7,10,11-triphenylene-hexa-yl, 2,3,7,8,12,13-truxene-hexa-yl, 2,3,6,7,10,11-tricycloquinazoline-hexa-yl, or 1,2,5,6,8,9,12,13-dibenzopyrene-octa-yl; X denotes a single bond, an oxygen atom, a sulfur atom, —OOC— or —COO—; R denotes a linear or branched alkyl group having 3–20 carbon atoms, of which at least 2 hydrogen atoms have been replaced with fluorine atoms and of which one methylene group can be replaced with an oxygen atom, a sulfur atom, —CH=CH— or —C≡C—; and n is an integer of 4, 6 or 8 corresponding to a valence of the group Ar. The discotic liquid crystal of the present invention is essentially different from the above-mentioned discotic liquid crystal compounds disclosed in Liquid Crystal having polyfluorinated side chains that include intermediate carboxyl (i.e., ester) groups.

The present invention further provides an organic electroluminescence device including a layer comprising the discotic liquid crystal of the present invention.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
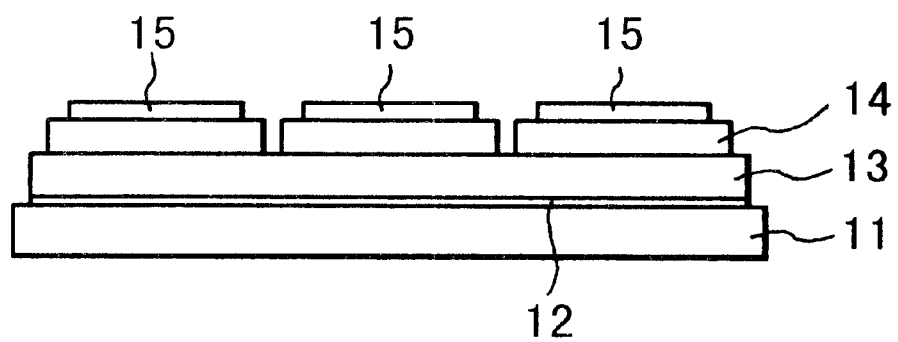
FIG. 1 illustrates an organization of an organic EL device according to an embodiment of the invention.
Figure 2:
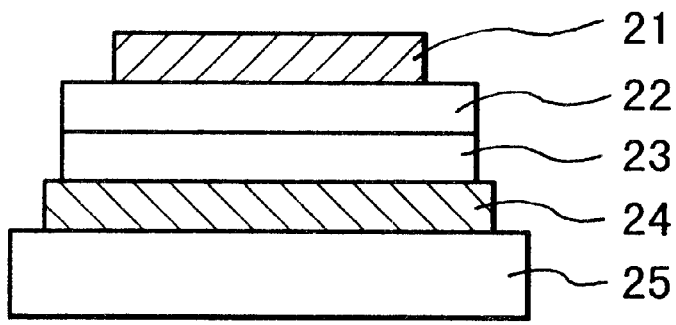
FIGS. 2 and 3 respectively illustrate a laminated structure of a conventional organic EL device.
Figure 3:
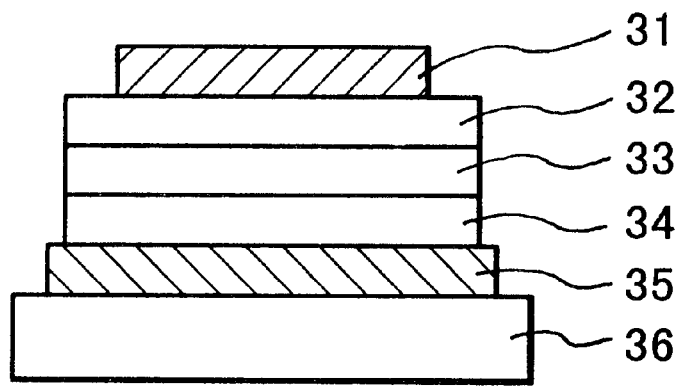

The discotic liquid crystal compound according to the present invention is a compound represented by formula (1) below:

Ar$-$(X$-$R)$_n$          (1)

In the above formula (1), Ar denotes a group of 2,3,5,6-benzoquinone-tetra-yl, 2,3,4,6,7,8-anthraquinone-hexa-yl, 2,3,6,7,10,11-triphenylene-hexa-yl, 2,3,7,8,12,13-truxene-hexa-yl, 2,3,6,7,10,11-tricycloquinazoline-hexa-yl, or 1,2,5,6,8,9,12,13-dibenzopyrene-octa-yl.

In view of the temperature range of liquid crystal phase, the group Ar is preferably 2,3,5,6-benzoquinone-tetra-yl, 2,3,4,6,7,8-anthraquinone-hexa-yl, 2,3,6,7,10,11-triphenylene-hexa-yl, or 1,2,5,6,8,9,12,13-dibenzopyrene-octa-yl; more preferably 2,3,6,7,10,11-triphenylene-hexa-yl, or 1,2,5,6,8,9,12,13-dibenzopyrene-octa-yl.

In the above formula (1), X denotes a single bond, an oxygen atom, a sulfur atom, —OOC— or —COO—. In view of the liquid crystal property, X is preferably an oxygen atom or —OOC—.

In the above formula (1), R denotes a linear or branched alkyl group having 3–20 carbon atoms, of which at least 2 hydrogen atoms have been replaced with fluorine atoms and of which one methylene group can be replaced with an oxygen atom, a sulfur atom, —CH=CH— or —C≡C—.

In view of the liquid crystal property of the resultant discotic liquid crystal, the group R may preferably be one of formula (i)–(vi), more preferably one of (i), (iii), (iv) and (vi), respectively shown below:

—(CH$_2$)$_e$—C$_f$F$_{2f+1}$,          (i)

wherein e and f are independently integers of 1 to 19 with the proviso that e+f=3 to 20;

—(CH$_2$)$_g$—(CF$_2$)$_h$—CF(C$_i$F$_{2i+1}$)C$_j$F$_{2j+1}$,          (ii)

wherein g, i and j are independently integers of 1 to 17 and h is an integer of 0 to 16 with the proviso that g+h+i+j=4 to 20;

—(CH$_2$)$_k$—(CF$_2$)$_p$H,          (iii)

wherein k and p are independently integers of 1 to 19 with the proviso that k+p=3 to 20;

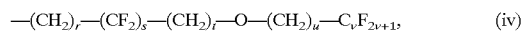

—(CH$_2$)$_r$—(CF$_2$)$_s$—(CH$_2$)$_t$—O—(CH$_2$)$_u$—C$_v$F$_{2v+1}$,          (iv)

wherein r, u and v are independently integers of 1 to 17, and s and t are independently integers of 0 to 16 with the proviso that r+s+t+u+v=3 to 19;

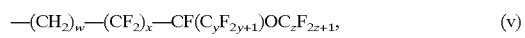

—(CH$_2$)$_w$—(CF$_2$)$_x$—CF(C$_y$F$_{2y+1}$)OC$_z$F$_{2z+1}$,          (v)

wherein w, y and z are independently integers of 1 to 17, and x is an integer of 0 to 16 with the proviso that w+x+y+z=4 to 19; and

—(CH$_2$)$_a$—(CF$_2$)$_b$—(CH$_2$)$_c$—O—C$_d$H$_{2d+1}$,          (vi)

wherein a, b and d are independently integers of 1 to 17, and c is an integer of 0 to 16 with the proviso that a+b+c+d=3 to 19.

In the above formula (1), n is an integer of 4, 6 or 8 corresponding to the valence of the group Ar, i.e., 4 for Ar of 2,3,5,6-benzoquinone-tetra-yl, 6 for Ar of 2,3,4,6,7,8-anthraquinone-hexa-yl, 2,3,6,7,10,11-triphenylene-hexa-yl, 2,3,7,8,12,13-truxene-hexa-yl and 2,3,6,7,10,11-tricycloquinazoline-hexa-yl, or 8 for Ar of 1,2,5,6,8,9,12,13-dibenzopyrene-octa-yl.

We have discovered that the discotic liquid crystal compound represented by the formula (1) has a stable and broad discotic liquid crystal phase and provides an organic EL device exhibiting stable and good luminescence characteristics.

Specific examples of discotic liquid crystal compounds according to the present invention (Example Compounds 1-1 to 1-100) are enumerated in Table 2 using the symbols A to F as examples of the skeleton group Ar shown in Table 1.

TABLE 1

| Symbol | Name of skeleton group | Structure |
| --- | --- | --- |
| A | 2,3,6,7,10,11-triphenylene-hexa-yl | 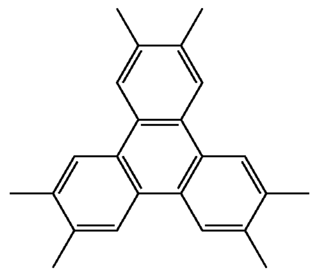 |
| B | 1,2,5,6,8,9,12,13-dibenzo-pyrene-octa-yl | 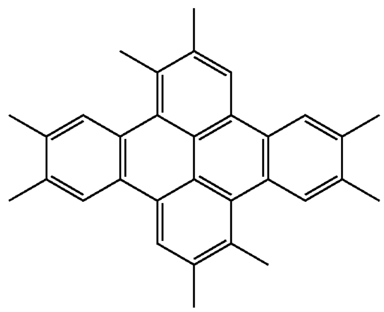 |
| C | 2,3,5,6-benzoquinone-tetra-yl | 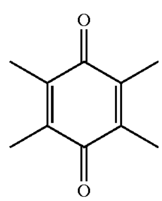 |
| D | 2,3,7,8,12,13-anthraquinone-hexa-yl | 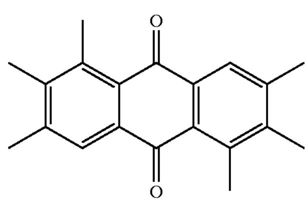 |
| E | 2,3,7,8,12,13-truxene-hexa-yl | 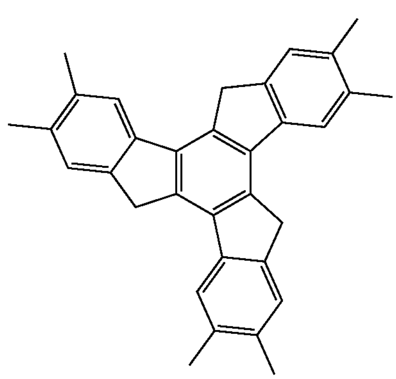 |

TABLE 1-continued

| Symbol | Name of skeleton group | Structure |
|--------|------------------------|-----------|
| F | 2,3,6,7,10,11-tricyclo-quinazoline-hexa-yl | (structure of hexamethyl-substituted tricycloquinazoline) |

TABLE 2

| No. | Ar | n | X | R |
|-----|----|----|----|---|
| (1-1) | A | 6 | — | $CH_2-O-(CH_2)_6C_3F_7$ |
| (1-2) | A | 6 | — | $CH_2-O-(CH_2)_8C_6F_{13}$ |
| (1-3) | A | 6 | O | $CH_2-C_2F_5$ |
| (1-4) | A | 6 | O | $(CH_2)_3-CF_3$ |
| (1-5) | A | 6 | O | $(CH_2)_6-C_2F_5$ |
| (1-6) | A | 6 | O | $(CH_2)_6-C_4F_9$ |
| (1-7) | A | 6 | O | $(CH_2)_8-C_3F_7$ |
| (1-8) | A | 6 | O | $(CH_2)_{10}-C_6F_{13}$ |
| (1-9) | A | 6 | O | $(CH_2)_{12}-C_8F_{17}$ |
| (1-10) | A | 6 | O | $(CH_2)_6-(CF_2)_2-CF(CF_3)_2$ |
| (1-11) | A | 6 | O | $(CH_2)_3-(CF_2)_3H$ |
| (1-12) | A | 6 | O | $(CH_2)_6-(CF_2)_2H$ |
| (1-13) | A | 6 | O | $(CH_2)_4-O-CH_2C_4F_9$ |
| (1-14) | A | 6 | S | $(CH_2)_{10}-O-CH_2C_6F_{13}$ |
| (1-15) | A | 6 | O | $(CH_2)_2-(CF_2)_3-(CH_2)_2-O-CH_2C_2F_5$ |
| (1-16) | A | 6 | O | $(CH_2)_3-(CF_2)_2-(CH_2)_3-O-CH_2C_4F_9$ |
| (1-17) | A | 6 | O | $CH_2CF(CF_3)OC_3F_7$ |
| (1-18) | A | 6 | O | $(CH_2)_3-(CF_2)_4-(CH_2)_3-O-CH_3$ |
| (1-19) | A | 6 | O | $(CH_2)_2-(CF_2)_9-(CH_2)_2-O-C_5H_{11}$ |
| (1-20) | A | 6 | OOC | $(CH_2)_2-CF_3$ |
| (1-21) | A | 6 | OOC | $(CH_2)_5-C_2F_5$ |
| (1-22) | A | 6 | OOC | $(CH_2)_7-C_3F_7$ |
| (1-23) | A | 6 | OOC | $(CH_2)_{11}-C_8F_{17}$ |
| (1-24) | A | 6 | OOC | $(CH_2)_5-(CF_2)_2H$ |
| (1-25) | A | 6 | OOC | $(CH_2)_8-O-CH_2C_6F_{13}$ |
| (1-26) | A | 6 | OOC | $CH_2(CF_2)_3-(CH_2)_2-O-CH_2C_2F_5$ |
| (1-27) | A | 6 | OOC | $(CH_2)_2-(CF_2)_4-(CH_2)_3-O-CH_3$ |
| (1-28) | A | 6 | COO | $(CH_2)_6-C_3F_7$ |
| (1-29) | A | 6 | COO | $(CH_2)_4-(CF_2)_3H$ |
| (1-30) | A | 6 | COO | $(CH_2)_5CF(CF_3)OC_3F_7$ |
| (1-31) | B | 8 | — | $CH_2-O-(CF_2)_3C_3F_7$ |
| (1-32) | B | 8 | O | $(CH_2)_3-C_3F_7$ |
| (1-33) | B | 8 | O | $(CH_2)_7-C_2F_5$ |
| (1-34) | B | 8 | O | $(CH_2)_6-C_4F_9$ |
| (1-35) | B | 8 | O | $(CH_2)_9-C_5F_{11}$ |
| (1-36) | B | 8 | O | $(CH_2)_{11}-C_7F_{15}$ |
| (1-37) | B | 8 | O | $(CH_2)_4-(CF_2)_3H$ |
| (1-38) | B | 8 | O | $(CH_2)_6-(CF_2)_4H$ |
| (1-39) | B | 8 | O | $(CH_2)_6-O-CH_2C_5F_{11}$ |
| (1-40) | B | 8 | O | $(CH_2)_8-O-CH_2C_5F_{13}$ |
| (1-41) | B | 8 | O | $(CH_2)_{10}-O-CH_2C_4F_9$ |
| (1-42) | B | 8 | O | $(CH_2)_3CF(CF_3)OC_2F_5$ |
| (1-43) | B | 8 | O | $(CH_2)_2-(CF_2)_4-(CH_2)_2-S-C_3H_7$ |
| (1-44) | B | 8 | OOC | $(CH_2)_3-C_2F_5$ |
| (1-45) | B | 8 | OOC | $(CH_2)_5-C_2F_5$ |
| (1-46) | B | 8 | OOC | $(CH_2)_9-C_6F_{15}$ |
| (1-47) | B | 8 | OOC | $(CH_2)_6-(CF_2)_4H$ |
| (1-48) | B | 8 | OOC | $(CH_2)_2-(CF_2)_2-(CH_2)_3-O-CH_2C_4F_7$ |
| (1-49) | B | 8 | COO | $(CH_2)_6-C_2F_5$ |
| (1-50) | B | 8 | COO | $(CH_2)_2-(CF_2)_3-(CH_2)_2-O-CH_2C_2F_5$ |
| (1-51) | C | 4 | — | $(CH_2)_3-O-(CH_2)_8C_4F_9$ |
| (1-52) | C | 4 | O | $(CH_2)_4-CF_3$ |
| (1-53) | C | 4 | O | $(CH_2)_6-C_2F_5$ |
| (1-54) | C | 4 | O | $(CH_2)_6-C_6F_{13}$ |
| (1-55) | C | 4 | O | $(CH_2)_{15}-C_5F_{11}$ |
| (1-56) | C | 4 | O | $(CH_2)_5-CF_2-CF(CF_3)_2$ |
| (1-57) | C | 4 | O | $(CH_2)_8-(CF_2)_4H$ |
| (1-58) | C | 4 | O | $(CH_2)_6-O-CH_2C_5F_{11}$ |
| (1-59) | C | 4 | O | $(CH_2)_2-(CF_2)_3-(CH_2)_2-O-CH_2C_3F_7$ |
| (1-60) | C | 4 | O | $CH_2C(CH_3)(CF_3)_2$ |
| (1-61) | C | 4 | OOC | $(CH_2)_8-C_7F_{15}$ |
| (1-62) | C | 4 | OOC | $(CH_2)_6-O-C_5F_{11}$ |
| (1-63) | C | 4 | OOC | $(CH_2)_3CF(CF_3)OC_2F_5$ |
| (1-64) | C | 4 | OOC | $(CH_2)_2-(CF_2)_3-(CH_2)_2-O-CH_3$ |
| (1-65) | C | 4 | COO | $(CH_2)_5-C_3F_7$ |
| (1-66) | D | 6 | — | $CH_2-O-(CH_2)_4C_5F_{10}H$ |
| (1-67) | D | 6 | O | $(CH_2)_6-C_4F_9$ |
| (1-68) | D | 6 | O | $(CH_2)_6-C_2F_5$ |
| (1-69) | D | 6 | O | $(CH_2)_{11}-C_8F_{17}$ |
| (1-70) | D | 6 | O | $(CH_2)_6-(CF_2)_8H$ |
| (1-71) | D | 6 | O | $(CH_2)_4-(CF_2)_2-CF(CF_3)_2$ |
| (1-72) | D | 6 | O | $CH_2CF_2CH_2-O-(CH_2)_6C_3F_7$ |
| (1-73) | D | 6 | O | $(CH_2)_3-O-(CH_2)_3C_6F_{13}$ |
| (1-74) | D | 6 | O | $(CH_2)_{10}CF(C_2F_5)OC_3F_7$ |
| (1-75) | D | 6 | O | $(CH_2)_4-CF_2-(CH_2)_4-O-C_4F_9$ |
| (1-76) | D | 6 | OOC | $(CH_2)_5-C_2F_5$ |
| (1-77) | D | 6 | OOC | $(CH_2)_3-(CF_2)_3-(CH_2)_4-O-CH_2CF_3$ |
| (1-78) | D | 6 | OOC | $(CH_2)_2-(CF_2)_2-(CH_2)_3-O-C_6H_{13}$ |
| (1-79) | D | 6 | OOC | $(CH_2)_6-(CF_2)_2-CF(CF_3)_2$ |
| (1-80) | D | 6 | COO | $(CH_2)_6-C_2F_5$ |
| (1-81) | E | 6 | — | $(CH_2)_5O(CH_2)_2-CF(CF_3)_2$ |
| (1-82) | E | 6 | O | $CH_2-CF_3$ |
| (1-83) | E | 6 | O | $(CH_2)_6-C_2F_5$ |
| (1-84) | E | 6 | O | $(CH_2)_6-(CF_2)_3-CF(CF_3)_2$ |
| (1-85) | E | 6 | O | $(CH_2)_3-(CF_2)_2H$ |
| (1-86) | E | 6 | O | $(CH_2)_3-(CF_2)_4-(CH_2)_3-O-CH_2C_3F_7$ |
| (1-87) | E | 6 | O | $(CH_2)_{10}-O-(CH_2)_3C_6F_{13}$ |
| (1-88) | E | 6 | OOC | $(CH_2)_2CH=CH(CH_2)_3C_8F_{17}$ |
| (1-89) | E | 6 | OOC | $(CH_2)_5-C_4F_9$ |
| (1-90) | E | 6 | OOC | $(CH_2)_2-(CF_2)_5-(CH_2)_3-O-C_5F_{11}$ |
| (1-91) | F | 6 | O | $(CH_2)_6-C_2F_5$ |
| (1-92) | F | 6 | O | $(CH_2)_2-C_4F_9$ |
| (1-93) | F | 6 | O | $CH_2-C_3F_7$ |
| (1-94) | F | 6 | O | $(CH_2)_4-O-CH_2C_3F_7$ |
| (1-95) | F | 6 | O | $(CH_2)_3-(CF_2)_5-(CH_2)_3-O-CH_2CF_3$ |
| (1-96) | F | 6 | O | $(CH_2)_2-(CF_2)_3-(CH_2)_2-O-C_2H_5$ |
| (1-97) | F | 6 | OOC | $(CH_2)_2-C\equiv C-(CH_2)_2-O-CH_2C_3F_7$ |
| (1-98) | F | 6 | OOC | $(CH_2)_3-(CF_2)_3H$ |
| (1-99) | F | 6 | OOC | $C_5F_{11}$ |
| (1-100) | F | 6 | COO | $CH_2CF_2CHFCF_3$ |

The organic EL device according to the present invention is characterized by using a novel discotic liquid crystal compound as mentioned above. The organic EL device may, for example, include a hole-transporting layer comprising the discotic liquid crystal compound of the present invention for hole transportation and also prevention of device deterioration, thereby exhibiting good luminescence performance.

EXAMPLES

The present invention will be described more specifically based on Examples.

Example 1

The above-indicated Example Compound 1-5 (2,3,6,7,10,11-hexakis[6-(perfluoroethyl)hexyloxy]-triphenylene) was prepared along the following scheme and in a manner described below.

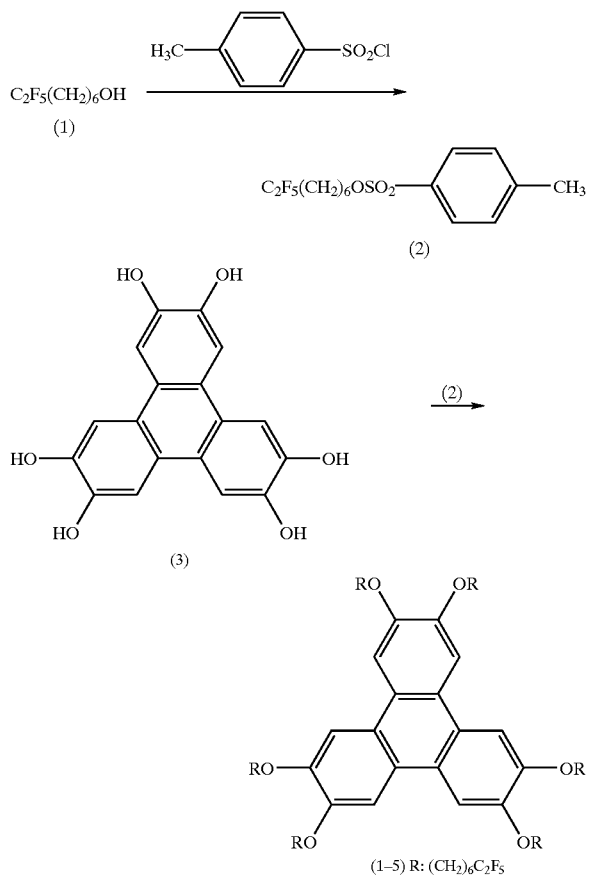

(1)→(2)

Into a reaction vessel, 5.00 g (22.7 mmol) of 6-(perfluoroethyl)hexanol (1) and 6.3 ml of pyridine were placed, and 5.21 g (27.3 mmol) of p-toluene-sulfonyl chloride was added little by little thereto under stirring and cooling with ice. After the addition, the system was stirred for 6 hours. The reaction product was poured into iced water, acidified by addition of 6 ml of hydrochloric acid and then extracted with chloroform. The organic layer was washed with salt water and dried with sodium sulfate, followed by solidification by removal of the solvent under a reduced pressure. The residue was purified by silica gel column chromatography with eluents of hexane/toluene=2/1, toluene, and toluene/ethyl acetate=5/1, successively, having increasing polarity, thereby obtaining 6.23 g (yield=73.3%) of 6-(perfluoroethyl)hexyl p-toluenesulfonate (2).

(3)→(1-5)

0.30 g (0.925 mmol) of 2,3,6,7,10,11-hexahydroxytriphenylene (3) was dissolved with 3 ml of DMF (dimethylformamide) in a 30 ml round-bottomed flask, and under stirring at room temperature, 0.27 g (6.75 mmol) of sodium hydride (60% in oil) was added little by little thereto. After the addition, the system was stirred for 10 minutes at room temperature and heated to ca. 80° C. on an oil bath, and 2.56 g (6.84 mmol) of 6-(perfluoroethyl)hexyl p-toluenesulfonate (2) dissolved in 2 ml of DMF was gradually added dropwise thereto. After the dropwise addition, the system was stirred for 5 hours under heating at the same temperature. After the reaction, the system was cooled to room temperature and stirred while adding chloroform and water thereto. The chloroform layer was condensed and purified by silica gel column chromatography with a chloroform eluent. After distilling off the chloroform, the resultant crystal was further purified by silica gel column chromatography with a toluene eluent and recrystallized from an acetone-methanol mixture solvent to obtain 0.52 g (yield=36.6%) of 2,3,6,7,10,1-hexakis[6-(perfluoro) hexyloxy]-triphenylene (1–5). The compound exhibited the following phase transition series.

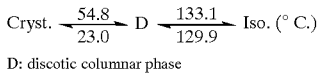

D: discotic columnar phase

The corresponding compound (R=C$_8$H$_{17}$) with no polyfluorination was reported to show the following transition series in Table 1 at page 309 of Destrade, C., et al., Mol. Cryst. Liq. Cryst., Vol. 65, pp. 307–314 (1981).

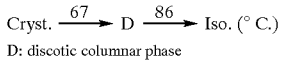

D: discotic columnar phase

From the above, Example Compound 1-5 according to the present invention showed a much broader discotic columnar phase temperature range than the corresponding compound with no polyfluorination.

Example 2

An organic EL device having a structure as shown in FIG. 1 was prepared by using the above-prepared Example Compound 1-5.

A 1.1 mm thick glass substrate 11 was coated with a 70 nm thick ITO film by sputtering, and the ITO film was surface-cleaned by irradiation with ultraviolet rays to form an anode (ITO) 12. Onto the anode 12, a 50 nm thick conductive liquid crystal layer 13 was formed by vacuum deposition of Example Compound (1-5) at a rate of 0.1 nm/sec under a vacuum of ca. 1×10$^{-5}$ Torr in a vacuum deposition apparatus.

On the liquid crystal layer 13, three types of luminescent organic layer segments of 50 nm were formed by vacuum deposition through a mask under conditions of three different materials, i.e., (i) Alq3 (tris(8-quinolinolato)aluminum) represented by formula (a) below alone, (ii) Alq3 (95 wt. %) doped with 5 wt. % of perylene represented formula (b) below for shifting the luminescence wavelength to a shorter wavelength, and (iii) Alq3 (95 wt. %) doped with 5 wt. % of DCM (a styryl dye) represented by formula (c) below for shifting to a longer wavelength side.

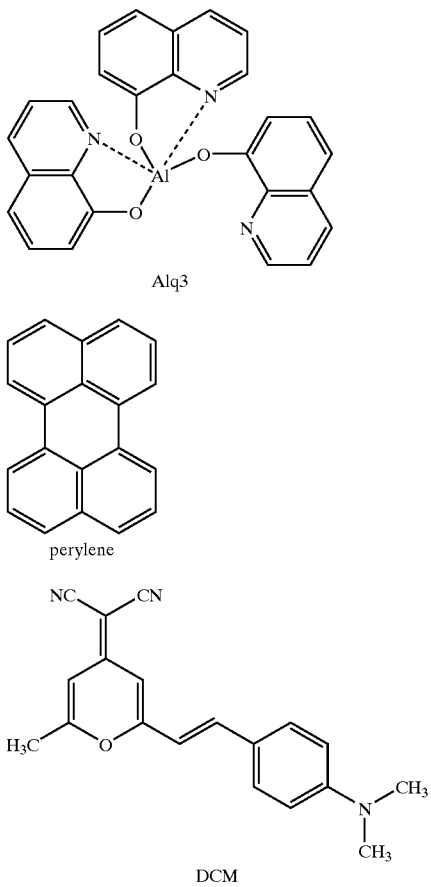

Alq3 perylene

DCM

The above-prepared luminescence layer segments were further coated with cathode segments 15, each comprising a 10 nm thick layer of Al—Li alloy electrode (Al: 98.2 wt. %, Li: 1.8 wt. %), and then with a 150 nm thick layer of Al electrode respectively by vacuum deposition to form an organic EL device having a structure as shown in FIG. 1.

The device was supplied with an electric field at an intensity of 10 volts/100 nm at various temperatures shown in Table 3 below, whereby increased luminescence intensities were observed at elevated temperatures in proportion with current densities at the respective temperatures shown also in Table 3 below.

TABLE 3

| Temperature (° C.) | Current density (mA/cm$^2$) |
|---|---|
| 30 | 0.0 |
| 40 | 1.5 |
| 50 | 11.0 |
| 80 | 10.0 |

During the drive at 50° C., the current value was gradually increased so that the liquid crystal presumably exceeded its phase transition temperature by current conduction heat. In this state, it was confirmed that the liquid crystal Compound 1-5 was aligned so that its discotic columns were aligned substantially vertical to the ITO electrode between the Alq3 layer and the ITO electrode. (The liquid crystal alignment was confirmed by a sample device having a corresponding structure except for a reduced cathode thickness of 10 nm by observation through a right-angle cross-nicol polarizing microscope. A similar alignment was observed at an increased liquid crystal layer thickness of 150 nm.) The increased current was also retained at 80° C.

In the vertical discotic column alignment state, the discotic liquid crystal Compound 1-5 has a π-electron resonance plane alignment substantially parallel to the adjacent electrode (ITO). Thus, by forming a carrier-transporting layer, wherein a discostic liquid crystal compound having a π-electron resonance structure is aligned so the its π-electron resonance plane is aligned substantially parallel to at least one electrode, it is possible to provide a luminescence device of which the luminescence performance has been stabilized presumably because of reduced diffusion of liquid crystal molecules into the luminescence layer.

As the luminescence was attained by lamination with a luminescence layer of Alq3 also having an electron-transporting characteristic, the discotic liquid crystal Compound 1-5 is considered to have a hole-transporting characteristic and was found to show a mobility of ca. $10^{-4}$ cm$^2$/Vs according to the TOF (time-of-flight) method (as described at Physical Review Letters, Vol. 70, No. 4, page 457).

Further, as polyfluorinated side chains are imparted to the liquid crystal, the liability of moisture contamination into the liquid crystal material can be reduced to thereby stabilize the device performance accompanied with current flow.

Thus, the discotic liquid crystal according to the present invention is effective for providing an organic EL device.

As described above, a discotic liquid crystal having a stable and broad discotic liquid crystal phase is provided by the present invention, and by using the liquid crystal compound, it is possible to provide an organic EL device having stable and good luminescence performance.

What is claimed is:

1. A discotic liquid crystal compound represented by formula (1) below:

$$Ar-(X-R)_n \quad (1),$$

wherein Ar denotes a group of 2,3,5,6-benzoquinone-tetra-yl, 2,3,4,6,7,8-anthraquinone-hexa-yl, 2,3,6,7,10,11-triphenylene-hexa-yl, 2,3,6,7,10,11-tricycloquinazoline-hexa-yl, or 1,2,5,6,8,9,12,13-dibenzopyrene-octa-yl;

wherein X denotes a single bond, an oxygen atom, a sulfur atom, —OOC— or —COO—;

wherein R denotes a linear or branched alkyl group having 3–20 carbon atoms, of which at least 2 hydrogen atoms have been replaced with fluorine atoms and of which one methylene group can be replaced with an oxygen atom, a sulfur atom, —CH=CH— or —C≡C—; and wherein n is an integer of 4, 6 or 8 corresponding to a valence of the group Ar.

2. The discotic liquid crystal compound according to claim 1, wherein Ar in the formula (1) denotes a group of 2,3,5,6-benzoquinone-tetra-yl, 2,3,4,6,7,8-anthraquinone-hexa-yl, 2,3,6,7,10,11-triphenylene-hexa-yl, or 1,2,5,6,8,9,12,13-dibenzopyrene-octa-yl.

3. The discotic liquid crystal compound according to claim 1, wherein Ar in the formula (1) denotes a group of 2,3,6,7,10,11-triphenylene-hexa-yl, or 1,2,5,6,8,9,12,13-dibenzopyrene-octa-yl.

4. The discotic liquid crystal compound according to claim 1, wherein X in the formula (1) is an oxygen atom or —OOC—.

5. The discotic liquid crystal compound according to claim 1, wherein R in the formula (1) is one of groups (i)–(vi) shown below:

$$—(CH_2)_e—C_fF_{2f+1}, \qquad (i)$$

wherein e and f are independently integers of 1 to 19 with the proviso that e+f=3 to 20;

$$—(CH_2)_g—(CF_2)_h—CF(C_iF_{2i+1})C_jF_{2j+1}, \qquad (ii)$$

wherein g, i and j are independently integers of 1 to 17 and h is an integer of 0 to 16 with the proviso that g+h+i+j=4 to 20;

$$—(CH_2)_k—(CF_2)_pH, \qquad (iii)$$

wherein k and p are independently integers of 1 to 19 with the proviso that k+p=3 to 20;

$$—(CH_2)_r—(CF_2)_s—(CH_2)_t—O—(CH_2)_u—C_vF_{2v+1}, \qquad (iv)$$

wherein r, u and v are independently integers of 1 to 17, and s and t are independently integers of 0 to 16 with the proviso that r+s+t+u+v=3 to 19;

$$—(CH_2)_w—(CF_2)_x—CF(C_yF_{2y+1})OC_zF_{2z+1}, \qquad (v)$$

wherein w, y and z are independently integers of 1 to 17, and x is an integer of 0 to 16 with the proviso that w+x+y+z=4 to 19; and $$—(CH_2)_a—(CF_2)_b—(CH_2)_c—O—C_dH_{2d+1}, \qquad (vi)$$

wherein a, b and d are independently integers of 1 to 17, and c is an integer of 0 to 16 with the proviso that a+b+c+d=3 to 19.

6. The discotic liquid crystal compound according to claim 5, wherein R in the formula (1) is one of the groups (i), (iii), (iv) and (vi).

7. An organic electroluminescence device including a layer comprising a discotic liquid crystal compound according to any one of claims 1 to 6.

* * * * *